US009662345B2

(12) United States Patent
Banov

(10) Patent No.: US 9,662,345 B2
(45) Date of Patent: *May 30, 2017

(54) ANTIBIOTIC COMPOSITION FOR INHALATION AND IRRIGATION

(71) Applicant: Professional Compounding Centers of America, Houston, TX (US)

(72) Inventor: Daniel Banov, Sugar Land, TX (US)

(73) Assignee: Professional Compounding Centers of America, Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,366

(22) Filed: Jun. 14, 2013

(65) Prior Publication Data

US 2014/0371166 A1     Dec. 18, 2014

(51) Int. Cl.
| A61K 31/7036 | (2006.01) |
| A61K 47/10 | (2006.01) |
| A61K 9/00 | (2006.01) |
| A61K 9/14 | (2006.01) |

(52) U.S. Cl.
CPC ........ *A61K 31/7036* (2013.01); *A61K 9/0075* (2013.01); *A61K 9/146* (2013.01); *A61K 47/10* (2013.01)

(58) Field of Classification Search
CPC .... A61K 31/7036; A61K 47/10; A61K 9/146; A61K 9/0075
See application file for complete search history.

(56) References Cited

U.S. PATENT DOCUMENTS

| 4,571,334 | A | * | 2/1986 | Yoshida et al. ............... 424/557 |
| 6,013,280 | A | | 1/2000 | Frisbee et al. |
| RE36,665 | E | | 4/2000 | Emanuele et al. |
| 6,161,536 | A | * | 12/2000 | Redmon ............... A61J 1/2093 128/200.14 |
| 7,368,102 | B2 | * | 5/2008 | Tarara et al. .................... 424/45 |
| 8,337,815 | B2 | | 12/2012 | Rairkar et al. |
| 2006/0013871 | A1 | * | 1/2006 | Berger ................. A61K 9/1635 424/464 |
| 2006/0073198 | A1 | * | 4/2006 | Boni et al. ..................... 424/450 |
| 2006/0115535 | A1 | * | 6/2006 | Lisa et al. ..................... 424/489 |
| 2010/0249240 | A1 | * | 9/2010 | Meadows et al. ............ 514/626 |
| 2011/0166149 | A1 | * | 7/2011 | Dellamary et al. ........... 514/249 |

FOREIGN PATENT DOCUMENTS

| EP | 0055041 B2 | 3/1982 |
| EP | 1124540 A1 | 8/2001 |
| EP | 1922150 A1 | 5/2008 |

OTHER PUBLICATIONS

Definition of solution, Merriam-Webster online dictionary, http://www.merriam-webster.com/dictionary/solution, accessed online on Dec. 22, 2015.*
Steckel et al., Int. J. Pharm., 2004, 278, p. 187-195.*
Brazeau et al., J. Pharm. Sci., 1998, 87(6), p. 667-677.*
Murray et al., Am. J. Respir. Crit. Care Med., 2011, 183, p. 491-499.*
New Lutrol product from BASF; Oct. 16, 2003; in-Pharma Technologist.com; Breaking News on Global Pharmaceutical Technology & Manufacturing; http://www.in-pharmatechnologist.com/content/view/print/168658; Aug. 5, 2015.
Lutrol L and Lutrol F-Grades, Technical Information; Apr. 2010; 03_100102e-03; 8 pages; Poloaxamers Ph. Eur., Poloxamer USP/NF; Poloxamers for Pharmaceutical Use; BASF Pharma Ingredients & Services.

* cited by examiner

*Primary Examiner* — Jonathan S Lau
(74) *Attorney, Agent, or Firm* — Gable Gotwals; David G. Woodral

(57) ABSTRACT

An antibiotic composition for the treatment of bacterial infections, especially in the respiratory tract is provided. The antibiotic composition may include a mixture of gentamicin as active pharmaceutical ingredient (API), and a micronized poloxamer composition as excipient. Micronized poloxamer composition may be produced by mixing poloxamer 188 and poloxamer 407 in a suitable apparatus where a low-frequency acoustic field may be applied to facilitate mixing. Antibiotic composition may be obtained in powder form, or in solution, and may be administered by inhalation or irrigation. In other embodiments, a topical formulation of the antibiotic inhalation or irrigation composition may be produced. In some embodiments, other suitable poloxamers, or sugar alcohols may be employed as excipients. Due to the synergistic effect of micronized poloxamer composition, antibiotic composition may provide improved solubility and bioavailability of gentamicin, thus decreasing side effects and time of treatment.

9 Claims, 1 Drawing Sheet

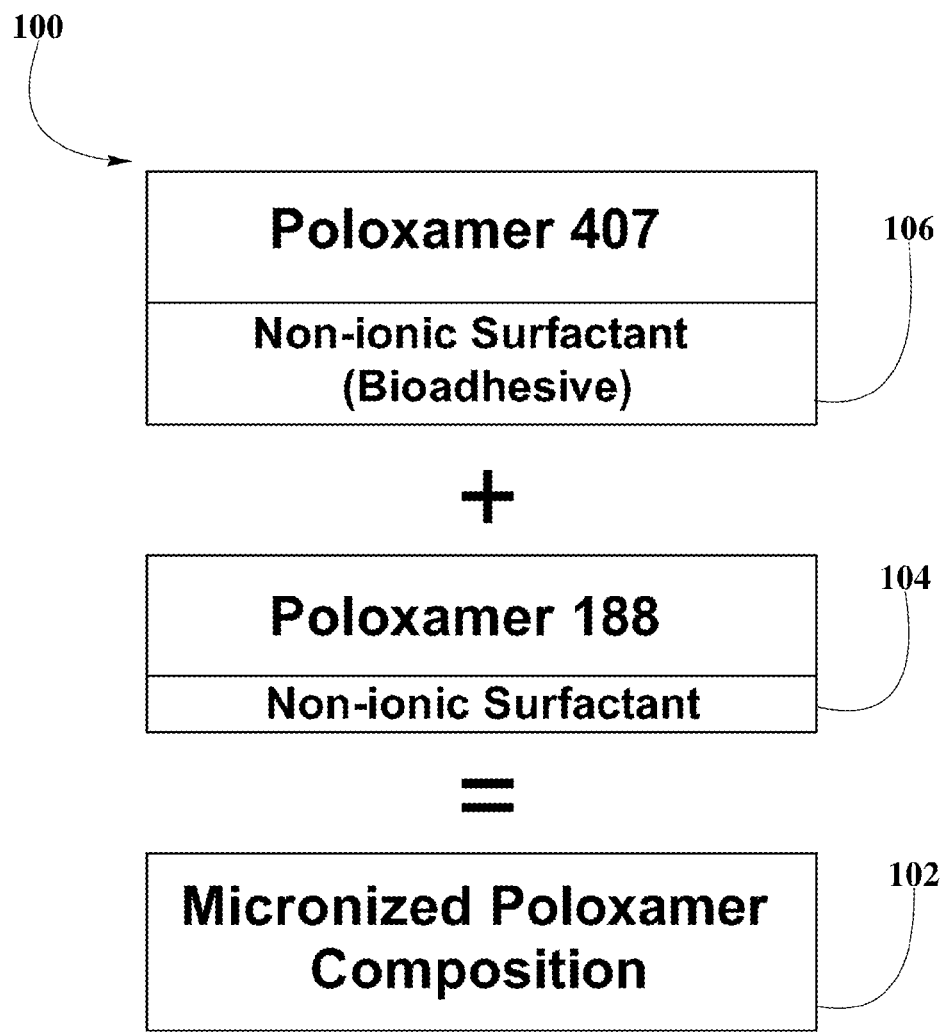

ANTIBIOTIC COMPOSITION FOR INHALATION AND IRRIGATION

CROSS-REFERENCE TO RELATED APPLICATIONS

N/A

BACKGROUND

Field of the Disclosure

The present disclosure relates in general to therapeutic formulations, and more particularly, to an inhalation and irrigation composition, such as nasal or wound irrigation, having gentamicin or any other suitable antibiotic.

Background Information

The administration of a drug by inhalation is called a local treatment effected by a direct application of the drug to the affected area and may be expected to produce fewer side effects as compared with the general administration of a drug. However, the application of a drug by inhalation to the respiratory apparatus inclusive of naris, throat, trachea and lung, may sometimes result in insufficient absorption of the drug through the mucous membrane depending upon the drug. Therefore, inhalation treatments are at a disadvantage in being unable to achieve enough indirect remedial effect attributable to an increase of the concentration of the drug in the blood. Additionally, it is impractical to administer some drugs by inhalation, as they irritate the mucous membrane, for instance of the respiratory tracts of the bronchi, causing coughing.

For the foregoing reasons, there is a need for drugs with increased absorption through the mucous membranes of the respiratory apparatus, improved dispersibility to the peripheral airways and alveoli, and which may have reduced side effects.

SUMMARY

The present disclosure may include a therapeutic formulation for the treatment of bacterial infections especially in the respiratory tract, and in wounds. The formulation may be employed as an antibiotic inhalation or irrigation composition. A method for preparing such composition is also described here.

The disclosed antibiotic inhalation or irrigation composition may include at least one antibiotic agent as active pharmaceutical ingredient (API) and a combination of two or more poloxamers as excipients. According to an embodiment, a suitable API may be gentamicin, while suitable poloxamers may include poloxamer 188 and poloxamer 407. Antibiotic inhalation or irrigation composition may include poloxamer 188 in concentrations of about 0.1% by weight to about 5% by weight, with about 1% by weight being preferred, poloxamer 407 in concentrations of about 0.1% by weight to about 5% by weight, with about 1% by weight being preferred.

According to an embodiment, a method for preparing antibiotic inhalation or irrigation composition is provided. The method may include combining suitable concentrations of poloxamer 188 and poloxamer 407 in an apparatus having a vessel where a low-frequency acoustic field is applied to improve mixing of the components, and produce micronized poloxamer composition. Afterwards, micronized poloxamer composition may be combined with gentamicin. The antibiotic inhalation or irrigation composition may be obtained in powder form and may be used to fill capsules, which may be later employed for inhalation or irrigation. In other embodiments, antibiotic inhalation or irrigation composition in powder form may be dissolved employing suitable solvents, such as sterile solution of sodium chloride and water, to obtain antibiotic inhalation or irrigation composition in solution form. Antibiotic inhalation or irrigation composition in solution form may be delivered to the respiratory tract using suitable devices such as aerosols, inhalers, and nebulizers, among others. According to other embodiments, gentamicin may be combined with micronized poloxamer composition to produce a topical formulation for the treatment of different bacterial infections.

The synergistic effect of micronized poloxamer composition, may provide improved solubility and bioavailability of gentamicin, thus decreasing treatment time and side effects occurrence. Antibiotic inhalation or irrigation composition may be used for treating bacterial infections caused by bacteria such as aerobic gram-negative rods, *Mycobacterium, Staphylococcus aureus* and certain species of *Streptococcus*, among others.

Numerous other aspects, features and benefits of the present disclosure may be made apparent from the following detailed description taken together with the drawing figures.

BRIEF DESCRIPTION OF THE DRAWINGS

The present disclosure can be better understood by referring to the following figures. The components in the figures are not necessarily to scale, emphasis instead being placed upon illustrating the principles of the disclosure. In the figures, reference numerals designate corresponding parts throughout the different views.

FIG. 1 is micronized poloxamer composition block diagram, according to an embodiment.

DETAILED DESCRIPTION

The present disclosure is here described in detail with reference to embodiments illustrated in the drawings, which form a part here. Other embodiments may be used and/or other changes may be made without departing from the spirit or scope of the present disclosure. The illustrative embodiments described in the detailed description are not meant to be limiting of the subject matter presented here.

DEFINITIONS

As used here, the following terms may have the following definitions:

"Active pharmaceutical ingredient (API)" refers to a substance that induces a suitable pharmacological or physiological effect, and may include agents with therapeutic, prophylactic, or cosmeceutical effects.

"Antibiotic" refers to an agent that destroys or inhibits bacterial growth.

"Excipient" refers to a substance added to a therapeutic formulation in order to provide suitable consistency or form the formulation.

"Microprilling" refers to a process where solid spherical microprills may be produced from liquid, tablets or encapsulated ingredients having a diameter of a few microns.

"Minimum Inhibitory Concentration (MIC)" may refer to the lowest concentration of an antimicrobial that may inhibit the visible growth of a microorganism after overnight incubation.

"Poloxamer" refers to a non-ionic triblock copolymer having surfactant properties. Poloxamers may be used as thickening agents, gel formers, co-emulsifiers, solubilizers, and consistency enhancers in creams and liquid emulsions.

DESCRIPTION OF THE DRAWINGS

The present disclosure may relate to a composition of ingredients that, in one embodiment may be an antibiotic composition. The composition may include a combination of two or more poloxamers as excipients and gentamicin as an active pharmaceutical ingredient (API). According to an embodiment, disclosed composition may be employed as an inhalation or irrigation formulation for the treatment of bacterial infections especially in the respiratory tract, and in wounds.

Poloxamer Composition

FIG. 1 is micronized poloxamer composition block diagram 100, according to an embodiment. The present disclosure may refer to an antibiotic inhalation or irrigation composition used for treating bacterial infections in the respiratory tract. The antibiotic inhalation or irrigation composition may include a micronized poloxamer composition 102 as excipient. According to some embodiments, micronized poloxamer composition 102 may include poloxamer 188 104 and poloxamer 407 106. Poloxamer 188 104 may be included in concentrations of about 0.1% by weight to about 5%, with about 1% by weight being preferred, and poloxamer 407 106 in concentrations of about 0.1% by weight to about 5%, with about 1% by weight being preferred.

Micronized poloxamer composition 102 may be manufactured in an apparatus where a low-frequency acoustic field may be applied, in order to facilitate the mixing process. Suitable concentrations of poloxamer 188 104 and poloxamer 407 106 may be deposited in a vessel which may be subjected to a low-frequency acoustic field in the axial direction, resulting in second order bulk motion of the fluid, known as particle collisions. Particles in the container may be excited by collisions with the vessel base and collisions with other particles in the container that may result in harmonic vibrations of the vessel with poloxamer 188 104 and poloxamer 407 106. The particle motions may be dependent upon the vibration amplitude, frequency, and the resultant accelerations that the particles undergo. The chaotic motions created within the mixing vessel may cause a great degree of particle-to-particle disorder, microcell mixing, as well as creating bulk mixing flow in the solid-solid systems. In order to manufacture micronized poloxamer composition 102, poloxamer 188 104 and poloxamer 407 106 may be mixed with a mixing length of about 50 μm, at a mechanical resonance of about 60 Hz.

Particle size of micronized poloxamer composition 102 may range between about 30 μm to about 70 μm, where about 50 μm may be preferred. The advantages of microprilling in micronized poloxamer composition 102 may include stronger solubilization properties, controlled dissolution rate, reduction of die-wall friction, achievement of homogeneous blend, elimination of dose dumping and effectiveness as water soluble lubricant.

Furthermore, antibiotic inhalation or irrigation composition may have solubility properties dictated by the hydrophobic portion of the poloxamers. The use of poloxamers may increase the solubility of the API that is employed, thus the drug may have enhanced treatment properties. Moreover, the properties of each poloxamer may vary in terms of molecular weight, appearance, hydrophilicity/hydrophobicity, and solubility, which may be determined by the chain length of the polyxyethylene (EO-) units and polyoxypropyene (PO-) units.

Gentamicin

A suitable antibiotic agent may be employed as an API. In an embodiment, micronized poloxamer composition 102 may be combined with gentamicin to produce antibiotic inhalation or irrigation composition. Antibiotic inhalation or irrigation composition may be efficient and effective in treating bacterial infections caused by bacteria such as aerobic gram-negative rods, *Mycobacterium, Staphylococcus aureus* and certain species of *Streptococcus*, among others. In some embodiments, gentamicin may be added to micronized poloxamer composition 102 in concentrations of about 20 mg to about 100 mg, with 80 mg being preferred.

Gentamicin is an aminoglycoside antibiotic obtained from cultures of *Micromonospora purpurea*, and is bactericidal in action. Similar to other aminoglycosides, gentamicin works by inhibiting bacterial protein synthesis through irreversible binding to the 30 S ribosomal subunit of susceptible bacteria. Gentamicin is actively transported into the bacterial cell where it binds to receptors present on the 30 S ribosomal subunit. This binding interferes with messenger RNA (mRNA). As a result, abnormal, nonfunctional proteins are formed due to misreading of the bacterial DNA. Eventually, susceptible bacteria die because of the lack of functional proteins.

Antibiotic Inhalation or Irrigation Composition having Gentamicin

Antibiotic inhalation or irrigation composition may be obtained in powder form. The powder may be employed to fill capsules, which may be used for inhalation or irrigation of the antibiotic composition. In other embodiments, antibiotic inhalation or irrigation composition in powder form may be dissolved in order to obtain antibiotic inhalation or irrigation composition in solution form. Suitable solvents may include sterile solution of sodium chloride, water, among others. Antibiotic inhalation or irrigation composition in solution form may include between about 2 ml to about 10 ml of solvent, and about 5 mg to about 5 g of antibiotic inhalation or irrigation composition, where about 1 g to about 2 g may be preferred. Additionally, micronized poloxamer composition 102 may optimize the particle distribution in inhalation or irrigation composition in solution form. According to an embodiment, when administered to humans, inhalation or irrigation composition may be delivered in amounts of about 2 ml to about 10 ml, where about 5 ml may be preferred.

The antibiotic inhalation or irrigation composition may be delivered to the respiratory tract employing suitable devices such as metered-dose inhalers (MDIs), dry powder inhalers, aerosols, capsules, and nebulizers, among others. By administering antibiotic inhalation or irrigation composition via inhalation, the drug may be driven directly into the respiratory tract and less is absorbed into the bloodstream, thus increasing bioavailability of the medication and decreasing treatment time. Additionally, the antibiotic inhalation or irrigation composition may be delivered by nasal irrigation employing saline nasal sprays, nebulizers, and the like. As well, antibiotic inhalation or irrigation composition in solution form may be employed for wound irrigation.

In other embodiments, gentamicin may be combined with micronized poloxamer composition 102 to produce a topical formulation. Topical formulation including gentamicin with micronized poloxamer composition 102 may be employed in the treatment of bacterial infection caused by bacteria such as *Staphylococcus aureus*, among others.

Furthermore, the synergistic effect of micronized poloxamer composition 102 may improve the solubility of the gentamicin, hence enhancing the action of the antibiotic inhalation or irrigation composition. Additionally, antibiotic inhalation or irrigation composition may reduce gentamicin's side effects, such as balance difficulty, unsteady vision, and tinnitus, among others.

Moreover, micronized poloxamer composition 102 may enhance gentamicin's properties by lowering the minimum inhibitory concentration (MIC) to about 1.7 g. The MIC was tested against microorganisms such as *Staphylococcus aureus*, and *Pseudomonas aeruginosa*, among others.

EXAMPLES

Example #1 is an embodiment of antibiotic inhalation or irrigation composition, where instead of employing poloxamer 188 104 and poloxamer 407 106 in micronized poloxamer composition 102, other suitable poloxamers may be used. Suitable poloxamers may include: poloxamer 101, poloxamer 105, poloxamer 108, poloxamer 122, poloxamer 124, poloxamer 181, poloxamer 182, poloxamer 183, poloxamer 184, poloxamer 185, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, poloxamer 334, poloxamer 335, poloxamer 338, poloxamer 401, poloxamer 402, poloxamer 403, and combinations thereof.

Example #2 is an embodiment of micronized poloxamer composition 102, where micronized poloxamer composition 102 may be used in combination with xylitol or sugar alcohol. Xylitol may be included in amounts of about 50% by weight to about 90% by weight, most suitable being 80% by weight.

Example #3 is an application of micronized poloxamer composition 102 in combination with any suitable APIs, such as gentamicin, which may be used for treating bacterial infections in animals, applying suitable dosages according to the weight and size of the animal.

While various aspects and embodiments have been disclosed here, other aspects and embodiments may be contemplated. The various aspects and embodiments disclosed here are for purposes of illustration and are not intended to be limiting, with the true scope and spirit being indicated by the following claims.

What is claimed is:

1. A composition for treating respiratory tract infections caused by bacteria, consisting of: a capsule including a powder mixture; a) said powder mixture including a gentamicin powder and b) a micronized powder composition consisting of between 0.1% by weight to 5% by weight poloxamer 188 and between 0.1% by weight to 5% by weight poloxamer 407.

2. The composition according to claim 1, wherein the poloxamer 188 is about 1% by weight.

3. The composition according to claim 1, wherein the poloxamer 407 is about 1% by weight.

4. An inhalation composition for treating respiratory tract infections caused by bacteria, consisting of: a powder mixture including a) a gentamicin powder and b) a micronized powder composition consisting of poloxamer 188 and poloxamer 407; and a solvent consisting of saline to form the inhalation composition.

5. A method for treating respiratory tract infections caused by bacteria, comprising dissolving a powder mixture including a) a gentamicin powder and b) a micronized powder composition consisting of poloxamer 188 and poloxamer 407 in a solvent consisting of water and sodium chloride to form an inhalation solution; and
administering to a patient in need of such treatment said inhalation solution.

6. The method according to claim 5, wherein the poloxamer 188 is about 0.1% by weight to about 5% by weight.

7. The method according to claim 5, wherein the poloxamer 188 is about 1% by weight.

8. The method according to claim 5, wherein the poloxamer 407 is about 0.1% by weight to about 5% by weight.

9. The method according to claim 5, wherein the poloxamer 407 is about 1% by weight.

* * * * *